United States Patent [19]

Fitjer

[11] Patent Number: 4,927,283
[45] Date of Patent: May 22, 1990

[54] APPLICATOR DEVICE WITH PUNCTURING MEANS

[75] Inventor: Holger Fitjer, Ansbach, Fed. Rep. of Germany

[73] Assignee: Georg Karl geka-brush GmbH, Bechhofen-Waizendorf, Fed. Rep. of Germany

[21] Appl. No.: 344,330

[22] Filed: Apr. 27, 1989

[30] Foreign Application Priority Data

Apr. 28, 1988 [DE] Fed. Rep. of Germany ....... 3814305

[51] Int. Cl.⁵ ...................... A47L 17/00; A61M 35/00
[52] U.S. Cl. .................................... 401/132; 401/134; 401/196; 401/207; 401/140; 604/3
[58] Field of Search ............... 401/207, 132, 133, 134, 401/135, 196, 140; 604/3

[56] References Cited

U.S. PATENT DOCUMENTS

| | | | |
|---|---|---|---|
| 1,607,768 | 11/1926 | Meusel | 401/132 X |
| 3,386,793 | 6/1968 | Stanton | 401/132 |
| 3,485,562 | 12/1969 | Hidden et al. | 401/196 X |
| 3,998,559 | 12/1976 | Hoyt | 401/132 |
| 4,148,318 | 4/1979 | Meyer | 401/134 X |
| 4,826,340 | 5/1989 | Rothweiler et al. | 401/140 X |

FOREIGN PATENT DOCUMENTS

| | | | |
|---|---|---|---|
| 49271 | 11/1938 | France | 401/133 |
| 1142591 | 9/1957 | France | 401/207 |
| 2001285 | 1/1979 | United Kingdom | 401/134 |
| 2160092 | 12/1985 | United Kingdom | 401/207 |

Primary Examiner—Steven A. Bratlie
Attorney, Agent, or Firm—Jordan and Hamburg

[57] ABSTRACT

An applicator device for the application of a liquid or pasty material includes a handle and an applicator detachably mounted on the handle, the applicator having a sealed chamber containing the liquid or pasty material. A manually operated release on the handle is operable to break the seal of the sealed chamber and to provide for release and application of such material from the applicator onto a desired site.

20 Claims, 1 Drawing Sheet

APPLICATOR DEVICE WITH PUNCTURING MEANS

BACKGROUND OF THE INVENTION:

The invention relates to an applicator device with a preferably porous applicator disposed on a handle and used for applying a liquid or a pasty composition which flows from a reservoir during application. The invention is especially suitable for cosmetic and medical uses.

Such applicator devices are already known, for example, as a shaving brush with a foam dispenser in the handle or as an appropriate tooth brush with toothpaste flowing via the handle and through a hole between the bristles, or finally also in the context of nail polish brushes, in which the nail polish likewise flows out of an inverted bottle directly between the brush bristles and thus can be spread on the fingernails. Finally, such applicator elements have also existed on a large scale for some years as shoe brushes.

With all these applicator devices, there exists the difficulty of sealing the reservoir from the outside, especially during times when the device is not being used. In addition, there is the considerable difficulty, for example, that the constant reuse of the same applicator for medical applications in conjunction with a larger reservoir conflicts with desirable health-related and hygienic criteria.

SUMMARY OF THE INVENTION:

It is therefore an object of the invention to provide an applicator that is suitable for applying liquids or pastes quickly, cleanly and simply and which is hygienic even when it is used for medical purposes.

Pursuant to the invention, this objective is accomplished by forming a preferably disposable, removable head component with a sealed dispenser chamber which is attached to a handle and which can be opened by means of a release device that can be activated from outside the handle, the release device being disposed in the handle.

The inventive head component holds only a relatively small supply for a single application. This eliminates the danger that the liquid or paste will suffer damage, dry out or otherwise become useless during the waiting period before renewed use. Furthermore, this mode of operation also provides the greatest possible guarantee for hygienic application, so that in this fashion it is possible to treat even contagious skin diseases or the like without problems, since the head component is discarded after a single use and replaced by a new head component when the need arises. To provide a larger than previously usual reservoir in the handle is more expensive or impractical for the application of high-grade liquids or pastes and especially for medical use, since in such a case a large portion of the composition to be applied dries up or otherwise becomes useless. In connection with medical uses, such multiple reuse is precluded for hygienic reasons. To this must finally be added the fact that, even with large reservoirs, the nature of the composition to be applied frequently prevents reuse of the applicator so that, in every case, at least the applicator would have to be replaced. Mass production of the inventive head components with a quasi-enlarged plug-in section of the applicator, the cavity of which accepts the amount of liquid or paste necessary for a single application, also is not substantially more expensive than manufacture of the applicators themselves. Moreover, the advantages of the inventive disposable unit more than compensate for possible additional costs.

Provision could be made for providing an opening in the applicator, the opening being closed off by a pin which protrudes on the opposite side in a handle, so that it need only be retracted slightly to allow the application composition previously sealed-off and stored in the interior of the head component to flow out. In a further development of the invention, provisions can be made with particular advantage so that the applicator is separated from the reservoir by its sealing foil which can be penetrated by a longitudinally movable mandrel disposed in the handle. The back side of the head component, which is to be fastened to the handle, has a sealed cover opening through which the mandrel passes.

After a new, still sealed head component is slipped onto the handle and immediately before use, the mandrel is pushed forwards, preferably with a longitudinally movable sliding plate mounted on the handle. The mandrel first encounters the sealed opening on the back side of the head component and then finally the sealing foil on the front side directly behind the actual applicator and punctures them. With that, the liquid can enter the applicator, through which it is distributed over the treatment site. After the treatment, the head component, which preferably is slipped onto the handle by means of a lock-in seat, is pulled off, discarded and replaced by a new, untouched head component for the next treatment case.

In a refinement of the invention, provision can be made so that the mandrel or the slide is acted upon by a return spring which holds it in its retracted position, so that minor carelessness with a new head component will not result in the destruction of the seals or the sealing foil which would cause the treatment composition to flow out prematurely. Provision can furthermore be made so that a longitudinal guide hole is provided at the front end of the handle. In its extreme retracted position, the mandrel extends into this hole under the action of the spring. Thus, when the slide plate is pushed forward, it is also made certain that the mandrel will penetrate the sealed opening on the back side of the head component without catching and will then, on the front side, penetrate the sealing foil to the applicator.

A refinement of the inventive applicator unit, which is especially easy to handle, is obtained through a further development of the invention owing to the fact that the head component has a front surface, which is inclined to the fastening surface and covered by an applicator in the form of foamed material plate. Such a plate-shaped foamed material applicator enables the treating composition to be dispensed uniformly. Moreover, due to the above-mentioned mutual slope of the surfaces, the plane of the applicator is inclined to the longitudinal axis of the handle so the handling is especially simplified.

Finally, it also falls within the scope of the invention to construct the head component in such a manner that it expands conically forwards towards the applicator. This results, on the one hand, in an applicator surface of a large area in conjunction with a thin handle that is advantageous to manipulate and, at the same time, in a sufficiently large reservoir capacity for the treatment composition.

Figure 1:
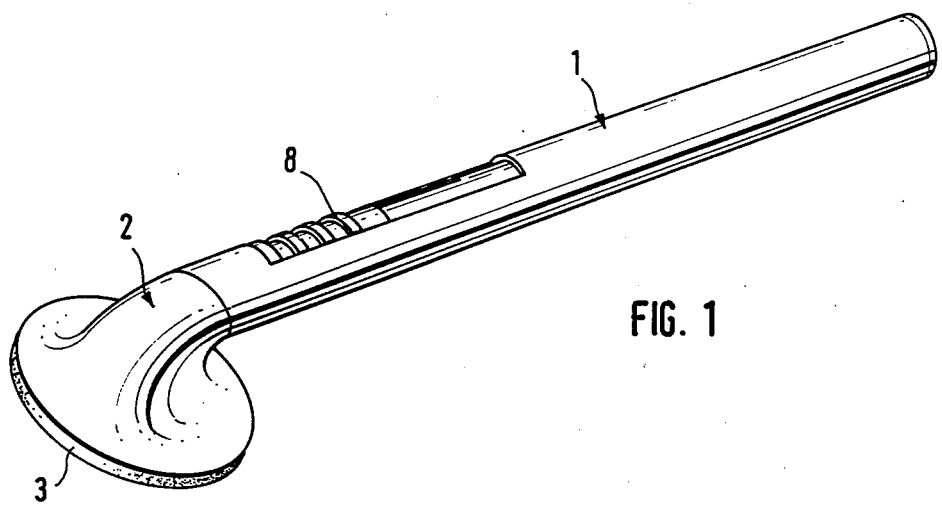
FIG. 1 is a perspective view of an inventive applicator device.
Figure 2:
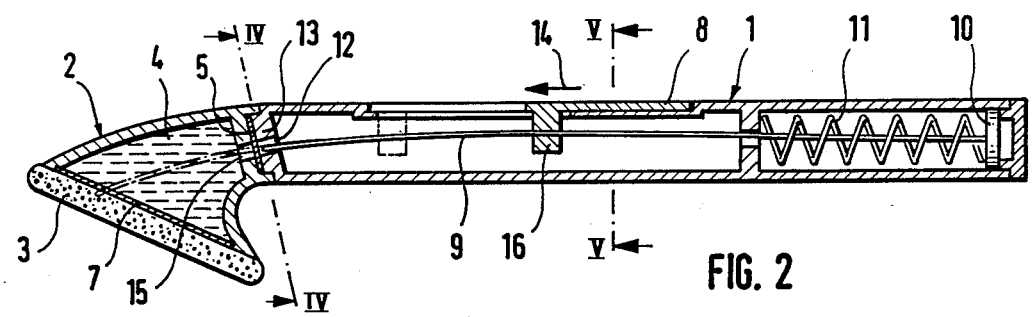
FIG. 2 is a longitudinal section through the applicator device of FIG. 1.
Figure 3:
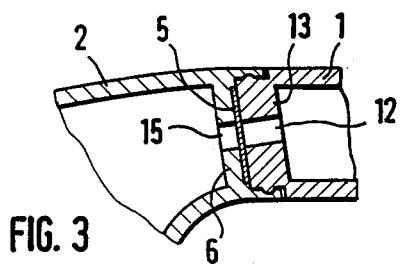
FIG. 3 is an enlarged partial sectional view through the transition region between the handle and the disposable head component, which is slipped on so that it can be detached.
Figure 4:
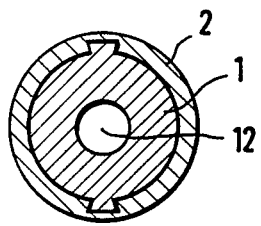
FIG. 4 is an enlarged cross-sectional view taken along the line IV—IV in FIG. 2

DESCRIPTION OF THE PREFERRED EMBODIMENTS:

The inventive applicator device comprises a handle 1 designed as a longitudinally extended stem, a head component 2 detachably connected thereto with a lock-in seat, and an applicator 3 which is designed in the embodiment shown as a flat member made of a foamed material. The head component 2 contains not only the applicator 3, but also a cavity 4 that serves as a reservoir for holding a liquid or pasty composition which is to be applied by means of the applicator 3 for cosmetic or medical uses. The composition is designed for a single application. For this purpose, the interior space 4 of the head component 2 is sealed. This seal is formed, on the one hand, with the help of a sealing foil 5 on the outside of the rear wall 6 which contacts the handle 1, and, on the other hand, by a foil 7 that is provided behind the applicator 3. To open the reservoir and deliver the liquid from the interior chamber 4 via the applicator 3, a mandrel 9 is connected to a slide plate 8 that is movably mounted on the handle 1. Through a plate 10, disposed at its interior end, the mandrel 9 is subjected to the action of a return spring 11. In the retracted position shown in FIG. 2, the front end of the mandrel protrudes into an elongated hole 12 of the front wall 13 of the handle 1. By these means, the mandrel 9 is forcibly guided so that, when the slide plate 8 is pushed forwards in the direction of the arrow 14, the mandrel 9 first penetrates the sealing foil 5 and then reaches the interior of the supply chamber 4 through a hole 15. Finally, as is shown in FIG. 2 by dots and dashes, it encounters the sealing foil 7 and punctures it, so that the liquid or pasty composition in the interior of the head component 2 can exit through this perforation into the applicator 3 and because of the porosity of the latter, reach the outside and finally, be distributed over the respective treatment site with the help of the applicator. After the contents of the head component have been discharged, the amount being designed so that it is exactly suitable for a single application, the head component 2, which is held on the handle 1 by a snap-in locking connection (see FIG. 3), is pulled off. For the next application, it is replaced by a new head component 2. The design is such that grooves (see FIG. 4) provide a certain disposition of the head component 2 with respect to the handle when the head component 2 is slipped on.

Figure 5:
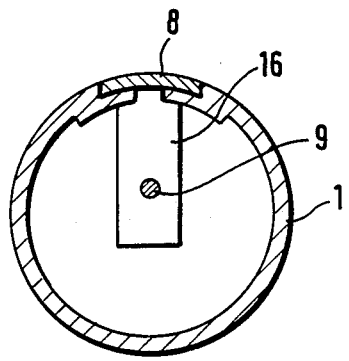
FIG. 5 is an enlarged sectional view taken approximately along the line V—V in FIG. 2.

FIG. 5 shows especially clearly the driving pin 16 of the slide plate 8 in which the mandrel 9 is mounted.

The slope of the plane of the applicator 3 with respect to the plane of the rear wall 6 of the head component 2 results in an angled design of the applicator device which guarantees especially convenient handling properties.

The invention is not limited to the example of the operation shown. Obviously, a number of other developments can be provided for the release of the liquid or pasty content of the head component when needed. The decisive point is that in the head component, designed so as to be disposable and mountable on an applicator, the amount needed for a single application is accommodated and can emerge to the outside by providing an opening.

I claim:

1. An applicator device for the application of a liquid or pasty substance, comprising a handle means having an interior chamber, an applicator means having a sealed compartment in which said liquid or pasty substance is sealed, detachable connecting means on said handle means and on said applicator means detachably connecting said applicator means to said handle means, said applicator means having at least a part thereof made of a penetrable material, a release means movably mounted in said interior chamber of said handle means between an extended and a retracted position, said handle means having an opening opening up into said interior chamber, said release means having an operable part extending into said opening and disposed to be engageable by the user of the applicator to move said release means between said extended and retracted positions, said release means being movable from its retracted to its extended position to penetrate said penetrable material and thereby effect release of said liquid or pasty substance from said sealed compartment, said release means in its retracted position being spaced from said applicator means to enable connection of said applicator means to said handle means by said detachable connecting means while said liquid or pasty substance remains sealed in said sealed compartment.

2. An applicator device for the application of a liquid or pasty substance, comprising a handle means having a handle housing, an applicator means having a sealed compartment in which said liquid or pasty substance is sealed, detachable connecting means on said handle means and on said applicator means detachably connecting said applicator means to said housing means, said applicator means having at least a part thereof made of a foil material, a release means movably mounted in said handle housing between an extended and a retracted position, said handle housing having an opening, said release means having an operable part extending into said opening and disposed to be engageable by the user of the applicator to move said release means between said extended and retracted positions, said release means being movable from its retracted to its extended position to penetrate said foil material and thereby effect release of said liquid or pasty substance from said sealed compartment, said release means in its retracted position being disposed to enable connection of said applicator means to said housing means by said detachable connecting means while said liquid or pasty substance remains sealed in said sealed compartment.

3. An applicator device according to claim 2, wherein said applicator means comprises an applicator housing having an opening sealed by said foil material, said release means being operable upon being moved from said retracted position to said extended position to penetrate said foil material to effect said release of said substance.

4. An applicator device according to claim 3, wherein said foil material comprises two foil members, said applicator housing having two openings each sealed by one of said foil members, said release means being operable to penetrate said foil members sealing each of said openings.

5. An applicator device according to claim 4, wherein said applicator means comprises an applicator pad juxtaposed to one of said foil members such that when the latter is penetrated by said release means, said substance flows past said penetrated one foil member to said applicator pad.

6. An applicator device according to claim 5, wherein said applicator housing has a wall having an aperture, the other of said foil members being disposed on said wall to seal said aperture.

7. An applicator device according to claim 5, wherein said applicator pad comprises a foamed plastic pad.

8. An applicator device according to claim 4, wherein each of said foil members are disposed on said applicator housing non-parallel relative to one another.

9. An applicator device according to claim 4, wherein said release means comprises an elongated mandrel longitudinally slidable in said handle means between said retracted and extended positions, said mandrel being slidable from said retracted position to said extended position to penetrate both of said foil members.

10. An applicator device according to claim 3, wherein said release means comprising an elongated mandrel longitudinally slidable in said handle means between said retracted and extended positions.

11. An applicator device according to claim 10, wherein said release means comprises biasing means in said handle housing biasing said mandrel in said retracted position.

12. An applicator device according to claim 10, wherein said operable part is connected to said mandrel.

13. An applicator device according to claim 10, wherein said handle housing has an end portion detachably connected to said applicator housing, and a guide means in said end portion for guiding said slidable mandrel.

14. An applicator device according to claim 10, wherein said mandrel is disposed in said handle housing when in said retracted position, said mandrel extending outside of said handle housing when in said extended position.

15. An applicator device according to claim 2, wherein said sealed compartment has a cross-section which progressively increases from one end to the other.

16. An applicator device according to claim 2, wherein said sealed compartment has a generally conical configuration.

17. An applicator device according to claim 2, wherein said applicator means has a first end portion and a second end portion, said first end portion being detachably connected to said handle means by said detachable connecting means, said second end portion having an applicator pad mounted thereon, said foil material comprising first and second foil members, said first foil member being disposed on said first end portion, said second foil member being disposed on said second end portion juxtaposed to said applicator pad, said release means being operable to penetrate both of said foil members.

18. An applicator device according to claim 17, wherein said handle housing has an end section connected to said first end portion of said applicator means, said end section of said handle housing having a first wall with a first aperture, said first end portion of said applicator means having a second wall with a second aperture, said first and second apertures being generally axially aligned.

19. An applicator device according to claim 18, wherein said first foil member on said first end portion is disposed between said first and second walls.

20. An applicator device according to claim 2, wherein said applicator means has a first detachable end portion and said handle means has a second detachable end portion, said applicator means being detachably mounted on said handle means at said first and second detachable end portions by said detachable connecting means.

* * * * *